United States Patent [19]

Hier et al.

[11] 4,246,350

[45] Jan. 20, 1981

[54] PROTEIN IMMOBILIZATION ON CHELATING RESINS

[75] Inventors: Deborah E. Hier, Stamford, Conn.; Patrick J. Oriel, Midland, Mich.

[73] Assignee: The Dow Chemical Company, Midland, Mich.

[21] Appl. No.: 16,587

[22] Filed: Mar. 1, 1979

[51] Int. Cl.$^3$ .............................................. C12N 11/08
[52] U.S. Cl. ................................ 435/180; 260/112 R; 435/94; 435/176; 435/234
[58] Field of Search ................. 435/94, 174, 180, 181, 435/176, 234; 423/24; 260/112 R

[56] References Cited

U.S. PATENT DOCUMENTS

| | | | |
|---|---|---|---|
| 3,794,563 | 2/1974 | Barker et al. ................ | 435/181 X |
| 3,912,593 | 10/1975 | Barker et al. ................ | 435/176 |
| 3,990,943 | 11/1976 | Bouniot et al. ............... | 435/94 |
| 4,025,389 | 5/1977 | Poulson et al. ............... | 435/94 |
| 4,098,867 | 7/1978 | Grinstead et al. ............ | 423/24 |

*Primary Examiner*—David M. Naff

[57] ABSTRACT

Proteins such as enzymes are immobilized on macroporous resins having recurring bis-picolylamine, imino diacetate or hydroxyethyl picolylamine chelating sites. Immobilization is carried out by contacting the resin with a multivalent metal ion selected from the transition metals or rare earth metals and adsorbing the protein to the resin. This immobilization technique permits strongly binding protein to a high surface area resin. The protein can be readily removed from the resin by simply flushing the resin with an appropriate solution.

7 Claims, No Drawings

PROTEIN IMMOBILIZATION ON CHELATING RESINS

BACKGROUND OF THE INVENTION

Various methods for immobilizing a protein on an insoluble support have been described. The insoluble support, which commonly is a polymer, may immobilize the protein by physical adsorption, covalent bonding, or by entrapment. The support may be a natural support such as cellulose or a synthetic support such as polystyrene. Covalent bonding between the protein and the support gives a conjugate which is not readily separable into its different components. Physical adsorption offers some advantages over chemical bonding where it is desirable to remove the bound protein from the support. This may occur where the support is used to remove the protein from a process stream, as for example in cleaning a waste stream, or where spent enzyme must be removed from the support and replaced with fresh enzyme as is necessary in certain commercial processes. The use of ion exchange resins to immobilize enzymes is well known (See for example U.S. Pat. No. 3,990,943). The use of chelating groups to bind protein is less well known (see U.S. Pat. Nos. 3,794,563 and 3,912,593).

SUMMARY OF THE INVENTION

The present invention is directed toward a method for immobilizing a protein on a macroporous resin support, preferably a styrene-divinylbenzene copolymer, having recurring chelating sites thereon which comprises a first step of contacting the copolymer with a multivalent metal ion selected from the transition metals or rare earth metals (lanthanum series) whereby a chelate is formed between the multivalent metal ions and the recurring chelating sites on the copolymer and a second step of immobilizing the protein on the copolymer. The present invention is further directed to a water insoluble polymer-protein conjugate comprising a macroporous resin support having recurring active sites which form a chelate with a multivalent metal ion selected from the transition metals or rare earth metals and a protein adsorbed thereon.

The macroporous resin supports used in the present invention are well known to persons skilled in the art, and in general consist of a water-insoluble polymer matrix which may be polymerized or copolymerized from monoethylenic and polyethylenic unsaturated monomers. Suitable resins for use in the present invention include macroporous styrene-divinylbenzene resins having recurring chelating sites thereon. Pore sizes of the resin may have diameters from about 50 angstroms to about 2000 angstroms with diameters greater than 200 angstroms being preferred. Particularly preferred are resins having imino diacetate or bis-picolylamine active chelating sites. Resins of this type will form chelates with multivalent metal ions selected from the transition metals or rare earth metals. Resin chelates formed with cobalt, nickel, ferrous or cupric ions have been found to satisfactorily bind protein thereto according to the present invention. Particularly preferred are resin chelates formed with members of the rare earth metals (lanthanum series of the periodic table). The present invention makes it possible to bind a protein to a resin bead having a high surface area in order to maximize the loading of the protein onto the support. The present invention has the further advantage of strongly binding the protein molecule to the support, yet the method described herein makes it possible to readily remove the protein by simply flushing the resin with an appropriate solution, for example with a salt solution.

Although the present binding method may be successfully used to immobilize most proteins the instant invention is especially useful to immobilize enzymes, i.e., a biologically active protein. Therefore the invention described herein may be used to immobilize commercially important enzymes such as glucose isomerase, protease, lipase, peroxidase, etc. during their use in chemical processes.

DETAILED DESCRIPTION OF THE INVENTION

Chelating resins used in the present invention contain recurring chelating groups, i.e., molecular groups capable of forming rings with a multivalent metal ion by means of co-ordinate bonds. Typical chelating groups which are satisfactory for use with the present invention include, but are not limited to, imino diacetate, bis-picoylamine, and hydroxyethylpicolylamine. Multivalent metal ions used to form the chelate may be selected from the transition metals, for example cobalt, nickel, manganese, ferric, and cuprous ions or most preferably from the lanthanum series, for example praseodynium and neodynium.

Although the pH need not be carefully controlled to effect adsorption between the chelate resin and the protein, it is generally preferred that the adsorption takes place at a selected pH to protect the protein. A controlled pH becomes particularly important when the protein is an enzyme which may be partially or totally inactivated by changes in pH. Therefore, the optimal pH for the adsorption to occur is dependent upon the pH requirements of the protein and not upon process limitations of the adsorption. The pH requirements of the enzymes and proteins of commercial interest are well known to those skilled in the art and will be dependent upon the specific protein used. Likewise, at temperatures above about 45°-50° C. most proteins will be denatured and the activity of enzymes is destroyed. Temperature in this method is limited by the requirements of the protein or enzyme and not by the requirements of the adsorption method. One of the advantages of this adsorption method relates to the mild conditions which may be used to effect coupling between the protein and the chelating resin. Some enzymes are able to act effectively at relatively high temperatures such as 70° to 80° C. The method disclosed herein may also be used to couple such heat resistant enzymes.

A number of proteins and enzymes have been used with the present invention. Protein coupling has been demonstrated using bovine serum albumin. The coupling of enzymes has been demonstrated using fumarase, glucose isomerase, alkaline protease, and horseradish peroxidase. The following examples will serve to further clarify the present invention, but are not to be costrued as a limitation thereon.

EXAMPLE 1

A macroporous styrene-divinylbenzene resin having recurring bis-picolylamine sites thereon was contacted with 10% aqueous cobalt chloride with stirring overnight at room temperature. The resin was washed with water, adjusted to pH 7.4, and dialyzed against 0.05 M Tris buffer pH 7.4. Four grams of the dialyzed resin was contacted with a glucose isomerase extract from an Actinoplane which contained approximately 2 international glucose isomerase units per ml of extract. The mixture was shaken in the cold for about one hour. The resin and immobilized enzyme was washed with about 700 ml of 0.05 M Tris buffer, pH 7.4. The enzyme activity was measured by the cysteine carbozole assay procedure and found to be 11.5 international glucose units per gm.

EXAMPLE 2

The binding of non-enzymatic protein was demonstrated using macroporous styrene-divinylbenzene resin beads having imino diacetate sites thereon in various salt forms. The resin was immersed in 2 ml of 0.1 M Tris buffer, pH 7.4, containing 2 mg/ml of bovine serum albumin. After 2 days at room temperature the amount of serum albumin removed from solution by the beads was analyzed by ultraviolet spectroscopy. The results appear in the Table below and indicate a number of salt derivatives were capable of binding the protein in significant quantity.

TABLE

| Bead Form | Protein (mg)/gm bead |
| --- | --- |
| $Co^{++}$ | 19 |
| $Pr^{+3}$ | 26 |
| $Ni^{++}$ | 16 |
| $Fe^{+3}$ | 16 |
| $H^+ - NA^+$ (Control) | 1.6 |

The data indicate the superior binding capacity of chelates formed from the lanthanum series, the preferred embodiment of the present invention.

The precise mechanism of the binding between the protein and the chelating resin is not understood, therefore the Applicants do not wish to limit their invention to a specific mechanism of adsorption. It is believed the protein binds to the active chelating sites where the metal ions are bound. As noted in the Table, binding does not occur in the absence of the metal ions.

We claim:

1. A process for immobilizing a protein on a macroporous styrene-divinylbenzene copolymer resin support having a pore size from about 50 angstroms to about 2000 angstroms in diameter and recurring bis-picolylamine, imino diacetate, or hydroxyethyl picolylamine chelating sites thereon which comprises a first step of contacting the resin support with a multivalent metal ion selected from the transition metals or rare earth metals whereby a chelate is formed between the multivalent metal ions and the recurring chelating sites on the copolymer and a second step of immobilizing the protein on the copolymer.

2. The process of claim 1 wherein the multivalent metal ions are selected from the rare earth metals.

3. A water-insoluble polymer-protein conjugate comprising a macroporous styrene-divinylbenzene copolymer resin support having a pore size from about 50 angstroms to about 2000 angstroms in diameter and active bis-picolylamine, imino diacetate, or hydroxyethyl picolylamine sites forming a chelate with a multivalent metal ion selected from the transition metals or rare earth metals and a protein adsorbed thereon.

4. The conjugate of claim 3 wherein the multivalent metal ion is selected from the rare earth metals.

5. The conjugate of claim 3 wherein the pore size of the macroporous resin is from about 200 angstroms and to about 2000 angstroms in diameter.

6. The conjugate of claims 3 or 6 wherein the protein is an enzyme.

7. Conjugate of claim 3 or 6 wherein the protein is glucose isomerase.

* * * * *

UNITED STATES PATENT AND TRADEMARK OFFICE
CERTIFICATE OF CORRECTION

PATENT NO. : 4,246,350
DATED : January 20, 1981
INVENTOR(S) : Deborah E. Hier, et al.

It is certified that error appears in the above-identified patent and that said Letters Patent are hereby corrected as shown below:

Column 4, Claim 6, "claims 3 or 6" should read --claims 3 or 4--.

Signed and Sealed this

Twenty-fifth Day of August 1981

[SEAL]

Attest:

Attesting Officer

GERALD J. MOSSINGHOFF

Commissioner of Patents and Trademarks